United States Patent
Cunningham et al.

(10) Patent No.: US 6,825,366 B2
(45) Date of Patent: Nov. 30, 2004

(54) PROCESS FOR THE EPOXIDATION OF OLEFINS USING GOLD-CONTAINING CATALYST

(75) Inventors: A. H. Derek Cunningham, Haarlem (NL); Harry Zumaqué, Bergisch Gladbach (DE); Daniel-Gordon Duff, Leverkusen (DE); Stephan Völkening, Köln (DE); Georg Wiessmeier, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 77 days.

(21) Appl. No.: 10/203,149

(22) PCT Filed: Jan. 25, 2001

(86) PCT No.: PCT/EP01/00809

§ 371 (c)(1),
(2), (4) Date: Aug. 6, 2002

(87) PCT Pub. No.: WO01/58585

PCT Pub. Date: Aug. 16, 2001

(65) Prior Publication Data

US 2003/0060643 A1 Mar. 27, 2003

(30) Foreign Application Priority Data

Feb. 7, 2000 (EP) .............................................. 00102558

(51) Int. Cl.⁷ .................... C07D 301/04; C07D 301/10; B01J 23/02; B01J 23/04
(52) U.S. Cl. ....................... 549/533; 549/513; 549/518; 549/523; 549/532; 502/243; 502/302; 502/344
(58) Field of Search ................................. 549/533, 513, 549/518, 523, 532; 502/243, 302, 344

(56) References Cited

U.S. PATENT DOCUMENTS

| | | | |
|---|---|---|---|
| 5,051,395 A | 9/1991 | Mitchell et al. | ............ 502/348 |
| 5,623,090 A | 4/1997 | Haruta et al. | ................ 568/360 |
| 5,932,750 A | 8/1999 | Hayashi et al. | ............. 549/523 |
| 5,939,569 A * | 8/1999 | Jones et al. | ................... 549/512 |
| 6,034,028 A | 3/2000 | Hayashi et al. | ............. 502/243 |
| 6,060,610 A | 5/2000 | Arca et al. | ................... 549/531 |
| 6,103,915 A | 8/2000 | Arca et al. | ................... 549/531 |

FOREIGN PATENT DOCUMENTS

| | | |
|---|---|---|
| DE | 44 47 231 | 7/1996 |
| DE | 198 04 712 | 8/1999 |
| EP | 266 015 | 5/1988 |
| EP | 850 936 | 7/1998 |
| WO | 98/00413 | 1/1998 |
| WO | 98/00414 | 1/1998 |
| WO | 98/30552 | 7/1998 |

OTHER PUBLICATIONS

Rodemerk et al, Chem. Ing. Tech., vol. 71, 1999, pp. 873–877.(English translation).*

* cited by examiner

*Primary Examiner*—Ba K. Trinh
(74) *Attorney, Agent, or Firm*—Joseph Gil; John E. Mrozinski, Jr.

(57) ABSTRACT

The invention is directed towards a process for the epoxidation of olefins, using molecular oxygen and hydrogen, characterized in that, as catalyst, a compound comprising gold, preferably in nanometer size, on a support material, in which the support material is comprised of Scandium, Yttrium, Lanthanide, Zirconium, Hafnium, Vanadium, Niobium, Tantalum, Chromium, Molybdenum and/or Tungsten and is essentially free of titanium is applied, and a compound comprising gold, preferably in nanometer size, on a support material, in which the support material is comprised of Scandium, Yttrium, Lanthanide, Zirconium, Hafnium, Vanadium, Niobium, Tantalum, Chromium, Molybdenum and/or Tungsten and is essentially free of titanium, a process for the preparation of said compounds and a method of catalyzing a chemical reaction through conducting said chemical reaction in the presence of said compound.

11 Claims, No Drawings

PROCESS FOR THE EPOXIDATION OF OLEFINS USING GOLD-CONTAINING CATALYST

BACKGROUND OF THE INVENTION

Direct gas phase partial oxidation of olefins by molecular oxygen to epoxides is long considered one of the most important reactions in commercial catalysis. Because of the importance of epoxides in the polyurethane industry, many attempts have been made to make epoxides by various means, some of which are commercialized. To produce epoxides from olefins containing more than two carbon atoms most production techniques use hydrogen peroxide or chlorohydrin as an oxidant. European patent (EP-A1-0 930 308) for example describes the use of ion exchanged titanium silicate for the production of epoxides in the presence of hydrogen peroxide, or chlorohydrin as the oxidant. More recently, U.S. Pat. No. 5,623,090 describes a new class of materials that may allow the direct production of epoxides such as propylene oxide directly from the olefin propylene using molecular oxygen, while in the co-presence of hydrogen. In this patent it is claimed that when gold is deposited on titanium, specifically anatase Titanium dioxide the direct gas phase partial oxidation of propylene to propylene oxide takes place.

Though the Au/titanium oxide system is still far from commercialization, and exhibits poor reaction yields, what separates gold from previous known inventions is the higher selectivities observed for the epxidation of olefins with 3 or greater carbons, an example of such being propylene. Silver based catalyst systems, for example, despite showing good yields and selectivities for ethylene oxide production, fail to give high or promising activities for propylene conversion. Subsequent patents since the work of Hayashi and Haruta (see Hayashi et al., Symposium on heterogeneous Hydrocarbon Oxidation, presented at the Div. Of Petroleum Chemistry, 211$^{th}$ National Meeting, American Chem. Soc., New Orleans, La., Mar. 24–29 1996) have therefore mainly concentrated on the use of gold in conjunction with Titanium WO 97/34692-A1, WO 98/00413-A1, WO 98/00414-A1. The exception is patent EP-A1-0 940 393, that employs gold in the co-presence of the element Zr.

Thus, the current understanding of the art is that the number of active species which can aid the partial oxidation of olefinic material is limited. Furthermore DE-A1-4447231 makes reference to the epoxidation power of Vanadium and Molybdenum specifically in the context of alkenes to glycols, polyols and glycol ethers, and not to the product propylene oxide. Similarly, documents claiming the element Molybdenum (PCT/EP97/05449), Vanadium, Tungsten. Chromium, Hafnium, and Tantalum (EP-A1–266 015) or Scandium (U.S. Pat. No. 5,051,395) to be promoters are likewise considered to be not valid in the context of gold based catalyst systems as the materials listed above, for example, Molybdenum, Vanadium and Scanadium are disclosed only in close connection with titanium as co-compounds.

SUMMARY OF THE INVENTION

The inventions described herein involve a process for the epoxidation of olefins, using molecular oxygen and hydrogen, characterized in that, as catalyst, a compound comprising gold, preferably in nanometer size, on a support material, in which the support material is comprised of Scandium, Yttrium, Lanthanide, Hafnium, Vanadium, Niobium, Tantalum, Chromium, Molybdenum and/or Tungsten. All catalysts operate free of the element Titanium. These findings are surprising, in light of the fact that in the last three years of intensive research only very few other catalyst systems containing gold have been discovered for the epoxidation reaction of olefins. The invention shows especially in the case of the Niobium and Tungsten systems which are preferred exceptionally high selectivities with respect to epoxidation, with the selectivity surprisingly improving with time. The invention also exhibits good stability of the catalysts over extended time periods.

Another object of the invention are compounds comprising gold, preferably in nanometer size, on a support material, in which the support material is comprised of Scandium, Yttrium, Lanthanide, Zirconium, Hafnium, Vanadium, Niobium, Tantalum, Chromium, Molybdenum and/or Tungsten.

Yet another object of the invention is a method of catalyzing a chemical reaction through conducting said chemical reaction in the presence of a compound comprising gold, preferably in nanometer size, on a support material, in which the support material is comprised of Scandium, Yttrium, Lanthanide, Zirconium, Hafnium, Vanadium, Niobium, Tantalum, Chromium, Molybdenum and/or Tungsten.

Yet another object of the invention is a process for the preparation of the invented compounds, characterized in that, gold particles of nanometer size are deposited on a support material in which the support material is comprised of Scandium, Yttrium, Lanthanide, Zirconium, Hafnium, Vanadium, Niobium, Tantalum, Chromium, Molybdenum and/or Tungsten.

Yet another object of the invention is a process for the preparation of the invented compounds, characterized in that, compounds comprising of gold particles of nanometer size on a support material in which the support material is comprised of Scandium, Yttrium, Lanthanide, Zirconium, Hafnium, Vanadium, Niobium, Tantalum, Chromium, Molybdenum and/or Tungsten are prepared via a sol-gel-process.

DETAILED DESCRIPTION OF THE INVENTION

As with many catalysts currently used in partial oxidation reactions, although any olefin can be used, the catalysts described within are apparently best able to activate the epoxidation of light olefins between C3 and C6, especially propene and butene. In the olefin the number of carbon-carbon double bonds contained is normally one but systems containing more than one can also be used. Examples to which the invention may be applied to include, ethylene, propylene, 1-butene, 2-butene, isobutylene 1-pentene, 2-pentene, butadiene, allyl alcohol, allyl chloride, styrene, cyclohexene and other materials of comparable likeness. The catalysts can also be used in epoxidation where more than one olefin is contained in the gas feed.

For use, the concentration of olefin contained in the reaction gas is considered to be not particularly critical and can be varied over a wide range. In most cases the composition of the gas will depend on the type of reactor used, the relative amount of oxygen and hydrogen used and if required, the amount of diluent added. For commercialization it is envisaged that the total olefin concentration present in the gas stream, entering the reactor, will vary, but is not limited, to between 5 to 80 mole percent, with the remainder of the gas, usually comprising of oxygen, hydrogen and an optional diluent gas.

The oxygen used in this process may come from any suitable source, such as air. However other sources of oxygen can be used such as nitrogen oxides or ozone. The invention can also function in the presence of hydrogen peroxide. The amount of oxygen required is dependent upon a number of parameters and may vary over a wide range, However, for best results the use of a olefin to oxygen molar ratio of greater than one is considered important. Often the selectivity is seriously reduced in the reactor if oxygen is present in large amounts, with the olefin undergoing either complete or partial oxidation. Typically the amount of oxygen present is usually between 1 and 20 mole percent, although other ratios may and can be used.

The source of hydrogen is also not considered important and may be supplied by any suitable source. By definition any suitable source may include such sources as molecular hydrogen obtained by alkane or alcohol dehydrogenation. The production of molecular hydrogen may be either carried out ex situ or in situ. Or in other words including within the reactor itself. The amount of hydrogen used depends on the amount required to convert the olefin to the corresponding epoxide and is thus variable. Normal operating ranges however suggest that the hydrogen concentration contained within the reactor should typically be below 30 mole percent, with the remainder comprising of oxygen olefin and diluent if required.

The addition of diluent is preferred, but is not essential for the reaction of the olefin to take place. The choice of diluent will depend on a number of parameters, including but not limited to safety, cost factors and inertness. Possible gases that could be used as a diluent are nitrogen, helium, argon or any other inert gas. As the process of transport of the reactants to the surface is the most essential parameter, the catalyst may also be employed in the liquid phase. In this case the liquid in which the catalyst is immersed should also be inert and aid as a good medium for transport of the reactant gases to the catalyst surface.

For the invention Vanadium can be introduced in any suitable form. Active catalyst have been obtained using $V_2O_5$, $VO_2$, $VCl_5$, $VCl_3$, Vanadium(IV)2,4-Pentanedionate, Vanadium(III)acetyl-acetonate, Vanadium(IV)bis(acetyl-acetonate)oxide and Vanadium(V)tri-propoxyoxide. In the case of Niobium based catalysts, the source of the Niobium species is again likewise diverse and includes $Nb_2O_5$, $NbO_2$, $NbCl_5$, and/or Niobium(V)n-butoxide. For the element Tungsten possible sources include Tungsten-(VI)chloride, Tungstic acid, Tungsten(VI)oxide, Tungsten(V)ethoxide. For scandium suitable non-limiting examples include Scandium chloride and Scandium acetate hydrate. For yttrium non-limiting examples include $Y_2O_3$, Yttrium(III)nitrate hexahydrate and Yttrium-2,4-Pentanedionate, for Lanthanum non-limiting examples include $La_2O_3$, Lanthanum(III) nitrate hexahydrate and Lanthanum-isopropoxide. For zirconium non-limiting examples include $ZrO_2$, Zirconium-2, 4-Pentanedionate, Zirconium(IV)propylate, Zirconiumoxide, Zirconium(IV)chloride and Zirconium-(IV)-i-propoxide, For Hafnium non-limiting examples include $HfO_2$, $HfCl_4$, Hafnium-2,4-Pentanedionate and Hafnium n-butoxide. For tantalum non-limiting examples include $Ta_2O_5$, Ta(V)ethoxide, Ta(V)methoxide and Tantalum(V)n-butoxide. For Chromium non-limiting examples are $CrCl_3*(H_2O)_6$, Tris(ethylene-diamine) chromium (III) chloride hemiheptahydrate and Chromium (III)-2,4Pentanedionate. For Molybdenum non-limiting examples include $MoCl_5$, $MoO_3$ and Molybdenum 2-4-pentanedionate. For the purpose of this invention, the actual source of the material is thus diverse and the choice of materials used will ultimately depend on the preparation method used that a further listing of compounds is deemed not to further enhance the understanding of the skilled artisan.

It is also possible to obtain activity form Au supported on any of the above mentioned metal systems that are diluted in silicates. Such non-limiting examples are ZSM-5; ZSM-11; ZSM-48 and MCM-41, or any materials of similar chemical or physical structures. One may also prepare active catalyst using gas phase routes, or preferably using standard sol-gel preparation routes known from e.g. L. C. Klein, Ann. Rev. Mar. Sci., 15, p. 227 and following (1985) or preferably those disclosed in DE-A-199 20 753.

As known in the art the above mentioned catalysts can be operated with all standard promoters, for example alkali metals, alkaline earth metals and/or all Lanthanide metals, excluding Lanthanum. For the purpose of this invention the element Lanthanum, though normally claimed to be a promoter for this reaction, is now considered to be a catalyst in its own right. It is thus specifically claimed that in the presence of gold the element Lanthanum is not a promoter, but a separate catalytic reactor. This invention is preferably directed to titanium-free compounds. It is however noted that one may reasonably use the mentioned elements as additives as promoters in catalyst not containing any of the elements claimed within this invention, if 1) the concentration of the element used is less than 1% of the active component of the alternative catalyst and 2) the elements Scandium, Yttrium Lanthanum, Hafnium, Vanadium, Niobium, Tantalum, Chromium, Molybdenum and/or Tungsten are not more active as measured by turnover frequency than the active part of the catalyst to which they are added.

Logically, if desired all above mentioned elements can be produced together in any combination to create so-called co-catalyst systems. The catalysts may also be included in or bound to other support materials that act to improve the physical properties of the system. Non limiting example are the use of a secondary support in order to impregnate the catalyst onto a monolith. Or supports that act to increase the total surface area exposed. Secondary supports may also be used to improve the physical properties such as to control coagulation. Non-limiting examples of such supports include silica, alumina, aluminasilicates, clays, carbonates, zeolites or any combination or mixture of the above.

Though not specific to the current invention it is known in the art that the catalysts can be used in any reactor capable of controlling and mixing the required oxygen, hydrogen and olefin. The reactor can be operated as batch, fixed bed, transport bed, fluidized bed and may be used as prepared or as a powder, or compressed pellets.

For this invention, in the case of the mentioned metals Scandium, Yttrium, Lanthanide, Zirconium, Hafnium, Vanadium, Niobium, Tantalum, Chromium Molybdenum, and Tungsten, the gold and metal loadings are variable. The gold particles in the current invention is observed to normally vary in size from 2 to 400 nm. It is however advisable that a high surface area is used for the highest possible conversions. For this reason gold particles of sizes between 1 and 10 nm are usually preferred. As a result typical gold loadings should usually be sufficiently low, i.e. typically below 0.1 atom percent, to facilitate the formation off the smaller nanometer (nm) size clusters. Catalyst comprising of gold with higher than 5 atom percent, though not considered to be optimal, may however be prepared. Techniques for depositing gold at nanometer sizes can be found in WO 98/00413-A1, WO 98/00414-A1, WO 98/00415-A1, WO 97/34692-A1; Haruta et al., J. Catal., 115 pp. 301–309 (1989); Tsubota et al. in "Preparation of Catalyst V" Stud. Surf. Sci. Catal., 63, eds., G. Poncelet et al., Elsevier, PP 695–704 (1991); Kobayashi et al, Sensors and actuators, B1 pp 222–225 (1990); Sakurai and Haruta, Catal. Today, 29 pp. 361 (1996); D. Cunningham et al. Res. Chem. Intermediates, 19 pp. 1–13 (1993); Okumura et al., Solid State Ionics, 95 143 (1997); D. Cunningham et al, Catal. Lett., 63 (1–2) pp. 43–47 (1999). As such any process for depositing a metal onto a solid support can be employed, for example impregnation, co-precipitation chemical vapor deposition, ion exchange techniques and deposition-precipitation. For catalyst preparation it is usually recommended that chlorine contamination be limited or avoided. A calcination step is usual, but not always required, and may be carried out either by rapid heat/quenching processing, or alternatively by long term exposure to a heating source. The temperature for calcination required depends on the preparation process but is usually not above 700° C.

One suitable method for obtaining active Au/Vanadium, Au/Niobium, and Au/Tungsten catalysts is that by sol-gel synthesis. In this process an alkoxide of the required metal is added to a suitable silanol compound, such as for example Tetra-ethylorthosilicate, Hexa-methyldisilazan, Tetra-decyloxysilane, Tetra-butoxysilane, Methyl-tri-ethoxysilane, Tetra-ethoxysilane, Tetra-methoxysilane, or essentially any other suitable silanol, including those containing benzene or more complex organic groups. The silanol is usually diluted in an alcohol such as ethanol, or propanal, butanol, or any suitable alcohol that is a liquid at the temperature of preparation. To this an acidic gold solution is added and the pH adjusted by the use of an acid. The resultant solution is typically homogeneous and forms a gel in which the gold is uniformly dispersed throughout. For the removal of chlorine it has been found adequate to simply heating the gel at elevated temperatures, such as at 350° C. However, for best results it is often best to wash the catalyst repeatedly in water that is free of chlorine or fluorine. The formation of metallic gold particles can occur at any temperature including and not excluding ambient room temperature. Promoters may be added to the catalysts to increase selectivity or yield, or alternatively to increase the operating life of the catalysts. Known examples include the alkali metals lithium, sodium potassium rubidium an/or Cesium. It is also known in the art that lanthanide rare earth metals and/or actinide metals which are not already claimed to be catalysts for epoxidation of olefins are often also useable for the purpose of promotion.

During operation it is envisaged that the invention will operate at a temperature from 20° C. to 250° C. The actual temperature used will depend upon such factors as; the reaction gas composition, or in the case of liquid reactors the freezing point of the fluid, the yield and degree of selectivity required, the pressure within the reactor, the reactor type used, the type of olefin present and any other parameter which may influence or require the need to modify the operating temperature. Pressure ranges from atmospheric to 200 bar are normally considered suitable. During operation with gaseous mixtures the gas flow-rate measured as a space velocity may vary and ultimately will depend upon the reaction parameters used.

Regeneration of the catalysts can be carried out by any one of a number of normal routines, such as high temperature treatment, or washing in a solution of neutral or acidic reagents (DE-A1–198 04 712).

EXAMPLES

All starting materials used below are commercially available.

Example 1

Catalysts Containing Vanadium (Catalyst A and B)

Catalyst A

To make a catalyst comprising of Au supported on Vanadium/tetraethylorthosilicate 2.92 ml of an alcohol such as ethanol is first mixed with 3298 mg Tetraethylorthosilicate. 0.202 grams of the vanadium compound, which for the purpose of this example is Vanadium(V)tri-propoxyoxid, is then added to the mixture. Vanadium can also be added as $VCl_3$, $V_2O_5$ or any other suitable chemical source. To this mixture 600 $\mu l$ $H_2O$ and 0.72 ml of 8 Mol/L HCl is then added. The sample is then mixed until gelation occurs. After gelation the sample is dried and heat treated at 350° C.

To load the gold, 1.0 grams of Vanadium silicate is added to 20 ml of water. To the suspension, 0.02 grams of Gold Chlorauric acid dissolved in 10 ml water is added and the system mixed for 1 hour. 10 ml of 0.015 molar sodium citrate is then added to the system and the system allowed to mix for a further 1 hour. The system is then removed and repeatedly washed with distilled water to remove chlorine, dried overnight at 100° C., 200 mbar and then finally calcined at 350° C.

After calcination, 500 mg of the catalyst A was then inserted into a gas reactor cell and studied at a temperature of 100° C. For this study a gas comprising 5.78% propylene 75.65% hydrogen 4.81% oxygen and 13.76% nitrogen diluant was passed through the bed at a flowrate of space velocity of 3500 ml $hr^{-1}$/gram.cat. The reaction products in the gas phase were analyzed by gas chromatography.

TABLE 1

| Catalyst A | Acetaldehyde | Propyleneoxide | Propionaldehyde | Acetone |
| --- | --- | --- | --- | --- |
| % conversion | 0.000 | 0.017 | 0.000 | 0.000 |

Table 1 Distribution of partial oxidation products obtained on passing propylene through catalyst A, comprising of Au, vanadium and Tetraethylorthosilicate (TEOS).

Catalyst B

To make a catalyst comprising of Au supported on Vanadium/tetraethylorthosilicate it is also possible to combine the gold during sol-gel preparation. 2.92 ml of an alcohol such as EtOH is first mixed with 3298 mg Tetraethylorthosilicate. 0.202 grams of the vanadium compound, which for the purpose of this example is Vanadium(V)tri-propoxyoxid, is then added to the mixture. Vanadium can also be added as $VCl_3$, $V_2O_5$ or any other suitable chemical source. To this mixture 600 $\mu l$ $H_2O$ and a 0.72 ml solution of 8 Mol/L HCl containing 20 mg $HAuCl_4$ is then added. The sample is then mixed until gelation occurs. After gelation the sample is dried and calcinated at 220 and 280° C. After calcination, 500 mg of each catalyst was then inserted into a gas reactor cell and studied under conditions similar to Catalyst A.

TABLE 2.1

| Vanadium | Au loading 0.1 Atom % | | Au loading 0.50 atom % | | Au loading 1.00 atom % | |
| --- | --- | --- | --- | --- | --- | --- |
| atom % | 220° C. | 280° C. | 220° C. | 280° C. | 220° C. | 280° C. |
| 1.0 | 0.048% | 0.050% | 0.036% | 0.040% | 0.034% | 0.040% |
| 5.0 | 0.081% | 0.076% | 0.053% | 0.074% | 0.064% | 0.074% |
| 10.0 | 0.000% | 0.000% | 0.008% | 0.002% | 0.012% | 0.063% |

Table 2.1 Percentage of propylene converted to the epoxide propylene oxide for catalysts comprising of Au, vanadium and Tetraethylorthosilicate (TEOS) prepared by the sol-gel technique, with gold concentrations between 0.05 to 1.00 atom percent gold and vanadium concentrations between 1 to 10 atom percent. Calcination temperatures are 220 and 280° C.

TABLE 2.2

|  | Catalyst containing 0.1 Atom % Au/5 Atom % V | | Catalyst containing 0.5 Atom % Au/5 Atom % V | | Catalyst containing 1.0 Atom % Au/5 Atom % V | |
| --- | --- | --- | --- | --- | --- | --- |
|  | 220° C. | 280° C. | 220° C. | 280° C. | 220° C. | 280° C. |
| Acetaldehyde | 0.0171 | 0.0216 | 0.0133 | 0.0183 | 0.0160 | 0.0263 |
| Propylene Oxide | 0.0806 | 0.0760 | 0.0533 | 0.0735 | 0.0642 | 0.0742 |
| Propion Aldehyde | 0.0215 | 0.0412 | 0.020 | 0.0292 | 0.0256 | 0.0338 |
| Acetone | 0.0146 | 0.0173 | 0.0116 | 0.0694 | 0.0141 | 0.0176 |

Table 2.2 Product distribution observed on passing propylene through catalysts comprising of Au, vanadium and Tetraethylorthosilicate (TEOS) prepared by the solgel technique, with gold concentrations between 0.05 to 1.00 atom percent gold and a vanadium concentration of 5 atom percent. Calcination temperatures for this invention were 220 and 280° C.

Example 2
Catalyst Containing Scandium (Catalyst C)

Catalysts comprising of elements from the transition metals series may in general be prepared by sol-gel/ deposition precipitation synthesis. This technique is generally adaptable to all elements. To make a catalyst comprising of Au supported on Scandium/tetraethylorthosilicate 2.92 ml of an alcohol such as ethanol is first mixed with 3298 mg Tetraethylorthosilicate. 0.126 grams of the Scandium compound, which for the purpose of this example is Scandium (III) chloride is then added to the mixture. To this mixture 1.67 g $HNO_3$ dissolved in 600 µl $H_2O$ is added and the sample mixed until gelation occurs. After gelation the sample is then dried, crushed into a powder and heated for 24 hours at 350° C.

To load the gold, 1.0 grams of the Scandium silicate produced above is added to 20 ml water. To the suspension, 0.02 grams of gold chlorauric acid, dissolved in 10 ml water, is added and the suspension mixed for 1 hour. 10 ml of 0.015 molar sodium citrate is then added to the system and the system allowed to mix for a further 1 hour. The wet powder is removed and repeatedly washed with distilled water to remove chlorine, dried overnight at 100° C., 200 mbar and finally calcined at 350° C.

Example 3
Catalyst Containing Chromium (Catalyst D)

Catalyst D was prepared in a manner identical to the preparation used to make catalyst B with the exception that $Cr(NO_3)_3.9H_2O$ was used in place of Vanadium (V) tripropoxide.

Example 4
Catalyst Containing Ytterbium (Catalyst E)

Catalyst E was prepared in a manner identical to C with the exception that $Y(NO_3)_3.6H_2O$ was used in place of Scandium (III) chloride.

Example 5
Catalyst Containing Zirconium (Catalyst F)

Catalyst F was prepared in a manner identical to C with the exception that Zirconium (IV) propylate was used in place of Scandium (III) chloride.

Example 6
Catalyst Containing Niobium (Catalyst G)

Catalyst G was prepared in a manner identical to C with the exception that Niobium (V) n-butoxide was used in place of Scandium (III) chloride.

Example 7
Catalyst Containing Molybdenum (Catalyst H)

Catalyst H was prepared in a manner identical to C with the exception that Molybdenum pentachloride was used in place of Scandium (III) chloride.

Example 8
Catalyst Containing Lanthanum (Catalyst I)

Catalyst I was prepared in a manner identical to C with the exception that $La(NO_3)_3.6H_2O$ was used in place of Scandium (III) chloride.

Example 9
Catalyst Containing Hafnium (Catalyst K)

Catalyst K was prepared in a manner identical to C with the exception that Hafnium n-butoxide was used in place of Scandium (III) chloride.

Example 10
Catalyst Containing Tantalum (Catalyst L)

Catalyst L was prepared in a manner identical to C with the exception that Tantalum (V) ethoxide was used in place of Scandium (III) chloride.

Example 11
Catalyst Containing Tungsten (Catalyst M)

Catalyst M was prepared in a manner identical to C with the exception that $WCl_6$ was used in place of Scandium (III) chloride.

TABLE 3

| Catalyst | | Acetaldehyde | Propylene Oxide | Propionaldehyde | Acetone |
| --- | --- | --- | --- | --- | --- |
| Cat. C | Conversion | 0.000 | 0.026 | 0.000 | 0.008 |
| 5 atom % Sc | Selectivity | 0.000 | 77.13 | 0.000 | 22.87 |
| Cat. D | Conversion | 0.051 | 0.007 | 0.043 | 0.002 |
| 5 atom % Cr | Selectivity | 49.29 | 6.69 | 42.03 | 1.98 |
| Cat. E | Conversion | 0.000 | 0.0035 | 0.000 | 0.001 |
| 5 atom % Y | Selectivity | 0.000 | 77.61 | 0.000 | 22.39 |
| Cat. F | Conversion | 0.004 | 0.030 | 0.004 | 0.003 |

TABLE 3-continued

| Catalyst | | Acetaldehyde | Propylene Oxide | Propionaldehyde | Acetone |
|---|---|---|---|---|---|
| 5 atom % Zr | Selectivity | 9.73 | 74.00 | 8.54 | 7.73 |
| Cat. G | Conversion | 0.000 | 0.05 | 0.000 | 0.000 |
| 5 atom % Nb | Selectivity | 0.000 | 100 | 0.000 | 0.000 |
| Cat. H | Conversion | 0.000 | 0.010 | 0.000 | 0.004 |
| 5 atom % Mo | Selectivity | 0.000 | 72.15 | 0.000 | 27.85 |
| Cat. I | Conversion | 0.000 | 0.006 | 0.000 | 0.004 |
| 5 atom % La | Selectivity | 0.000 | 62.63 | 0.000 | 37.37 |
| Cat. K | Conversion | 0.000 | 0.013 | 0.000 | 0.016 |
| 5 atom % Hf | Selectivity | 0.000 | 44.58 | 0.000 | 55.42 |
| Cat. L | Conversion | 0.000 | 0.153 | 0.004 | 0.001 |
| 5 atom % Ta | Selectivity | 0.000 | 96.37 | 2.70 | 0.93 |
| Cat. M | Conversion | 0.000 | 0.01 | 0.000 | 0.000 |
| 5 atom % W | Selectivity | 0.000 | 100 | 0.000 | 0.000 |

Table 3: Distribution of partial oxidation products obtained on passing propylene through catalyst comprising of 1.0 atom % Au, Tetraethylorthosilicate (TEOS) and 5 atom % transition metal, prepared by sol-gel/depostion precipitation techniques.

Example 12

Numerous methods are known within the art that may act to increase the total surface area of the catalyst to increase the total exposure area and to reduce the size of the supported gold particles. One such method is the addition of a secondary additive to cause fragmentation of the sol-gel. A specific, but non-limiting example is the addition of Trivinylmethoxysilane to tetraethylorthosilicate.

To make a catalyst comprising of Au supported on Trivinylmethoxysilane modified Molybdenum/tetraethylorthosilicate 2.92 ml of an alcohol such as ethanol if first mixed with 3403 mg Tetraethylorthosilicate and 23 mg of Trivinylmethoxysilane. 45.5 mg of the Molybdenum compound, which of the purpose of this example is $MoCl_5$, is then added to the mixture. To this mixture 600 μd $H_2O$ smf 0.72 ml 1.67 g of 63% $HNO_3$ is then added. The sample is then mixed until gelation occurs. After gelation the sample is dried over 3 days and heat treated at 600° C.

To load the gold, 1.0 grams of Molybdenum silicate is added to 20 ml of water. The solution is then heated to 70° C. and, while stirring, to the suspension 0.02 grams of $HAucl_4$ dissolved in 10 ml water is added dropwise over a period of 15 minutes. The pH is then modified to 7. To the suspension 10 ml of a pH 7 modified 0.015 ml/L sodium citrate solution is added and the system mixed for 1 hour at a pH of 7. The sample is then washed thoroughly several times in distilled water to remove chlorine, dried overnight at 100° C., 200 mbar and then finally calcined at 150° C.

After calcination, 500 mg of the catalyst was then inserted into a gas reactor cell and studied at a temperature of 140° C. For this study a gas comprising of 5.78% propylene, 75.65% hydrogen, 4.81% oxygen and 13.76% nitrogen dilutant was passed through the bed at a flowrae of space velocity of 3500 ml $hr^{-1}$/gram.cat. Analysis of the reaction products in the gas phase were analysed by gas chromatography (see Table 4).

TABLE 4

| Catalyst | | Acetalde-hyde | Propylene Oxide | Propion-aldehyde | Acetone |
|---|---|---|---|---|---|
| Cat. 1 atom % Mo | Conversion | 0.0487 | 0.875 | 0.0448 | 0.010 |
| | Selectivity | 4.97 | 89.37 | 4.57 | 1.09 |

What is claimed is:

1. A process comprising:
    epoxidizing
    (a) at least one olefin; in the presence of
    (b) at least one oxygen source;
    (c) at least one hydrogen source; and
    (d) at least one catalyst comprising:
        (i) at least one support material which contains one or more elements chosen from Scandium, Hafnium, Vanadium, Niobium, Tantalum, Chromium, Molybdenum and Tungsten; and
        (ii) gold
    wherein the at least one catalyst is tree of titanium.

2. The process of claim 1 in which the gold is in the form of particles between 1 and 10 nm in size.

3. The process of claim 1 in which the olefin is propene.

4. A noble-metal containing catalyst comprising:
    (i) at least one support material which contains one or more elements chosen from Scandium, Hafnium, Vanadium, Niobium, Tantalum, Chromium, Molybdenum and Tungsten; and
    (ii) gold wherein the at least one catalyst is free of titanium.

5. The catalyst of claim 4 in which the gold is in the form of particles between 1 and 10 nm in size.

6. A process comprising:
    depositing
    (i) gold;
    on
    (ii) at least one support material which contains one or more elements chosen from Scandium, Hafnium, Vanadium, Niobium, Tantalum, Chromium, Molybdenum and/or Tungsten;
    in a manner such that a catalyst is formed wherein the at least one support material is free of titanium.

7. The process of claim 6 in which the gold is in the form of particles between 1 and 10 nm in size.

8. A process of making a catalyst comprising:
    depositing by a sol-gel process
    (i) gold;
    on (ii) at least one support material which contains one or more elements chosen from Scandium, Hafnium, Vanadium, Niobium, Tantalum, Chromium, Molybdenum and/or Tungsten;

in a manner such that a catalyst is formed wherein the at least one support material is free of titanium.

9. In a process for the epoxidation of an olefin in the presence of at least one oxygen source and at least one hydrogen source, the improvement comprising conducting the epoxidation of the olefin in the presence of the noble metal-containing catalyst made according to the process of claim 6.

10. The process of claim 9 in which the gold is in the form of particles between 1 and 10 nm in size.

11. The process of claim 8 in which the gold is in the form of particles between 1 and 10 nm in size.

* * * * *